United States Patent [19]

Yeh et al.

[11] Patent Number: 4,560,804

[45] Date of Patent: Dec. 24, 1985

[54] CATALYTIC PROCESS FOR THE MANUFACTURE OF KETONES

[75] Inventors: Chuen Y. Yeh, Edison; Charles Savini, Warren, both of N.J.

[73] Assignee: Exxon Research & Engineering Co., Florham Park, N.J.

[21] Appl. No.: 516,537

[22] Filed: Jul. 25, 1983

Related U.S. Application Data

[63] Continuation-in-part of Ser. No. 420,525, Sep. 21, 1982, abandoned, and Ser. No. 420,526, Sep. 21, 1982, abandoned, and Ser. No. 420,648, Sep. 21, 1982, abandoned, and Ser. No. 420,716, Sep. 21, 1982, abandoned.

[51] Int. Cl.$^4$ .................. C07C 45/34; C07C 45/42
[52] U.S. Cl. .................. 568/408; 568/400; 568/401; 568/360; 568/365; 568/320; 568/309; 568/361; 568/404; 568/403; 568/69; 568/899; 568/900
[58] Field of Search ............ 568/408, 365, 401, 360, 568/320, 309, 400

[56] References Cited

U.S. PATENT DOCUMENTS

| | | | |
|---|---|---|---|
| 2,523,686 | 5/1947 | Engel | 260/597 |
| 3,600,443 | 8/1971 | Covidall et al. | 260/604 |
| 3,993,593 | 11/1976 | Kaneko et al. | 252/441 |
| 4,260,553 | 4/1981 | Happel et al. | 260/449 |

FOREIGN PATENT DOCUMENTS

| | | |
|---|---|---|
| 59179 | 3/1947 | Netherlands . |
| 876024 | 1/1958 | United Kingdom . |
| 1029175 | 5/1963 | United Kingdom . |

OTHER PUBLICATIONS

R. A. Acuna et al., Anales de Quimica 1978, supp. 1, pp. 17–23.

*Primary Examiner*—James H. Reamer
*Attorney, Agent, or Firm*—Jack B. Murray, Jr.

[57] ABSTRACT

An improved process is provided for forming ketones from the corresponding olefins by vapor phase oxidation of the olefin in the presence of water vapor, and optionally in the additional presence of molecular oxygen employing a heterogeneous catalyst comprising at least one member selected from the group consisting of Ce, Nd and La and compounds and complexes thereof, optionally containing at least one metal compound or complex selected from the group consisting of Group VIB metals and Group VIII noble metals, and mixtures thereof. It has been surprisingly found that these catalysts effect the formation of ketones in high selectivities with minimal selectivities to the undesirable carbon dioxide and carbon monoxide by-products.

13 Claims, No Drawings

CATALYTIC PROCESS FOR THE MANUFACTURE OF KETONES

CROSS-REFERENCE TO RELATED APPLICATIONS

This application is a Continuation-in-Part of our co-pending applications Ser. Nos. 420,525; 420,526; 420,648 and 420,716, all filed on Sept. 21, 1982, all now abandoned and related to our applications filed on even date herewith; entitled "Improved Catalysts and Process for Conversion of Olefins to Ketones", which is a Continuation-in-Part of Ser. No. 420,527, filed on Sept. 21, 1982; entitled "Improved Catalysts and Process for Conversion of Olefins to Ketones" now abandoned, which is a Continuation-in-Part of Ser. No. 420,626, filed on Sept. 21, 1982; and entitled "Improved Catalytic Process for the Conversion of Olefins to Ketones" now abandoned, which is a Continuation-in-Part of Ser. No. 420,715 and Ser. No. 420,627, both filed on Sept. 21, 1982 both now abandoned.

BACKGROUND OF THE INVENTION

1. FIELD OF THE INVENTION

This invention relates to process and catalyst useful in the manufacture of ketones from olefins, and more particularly to lanthanide-containing catalysts useful in the vapor phase conversion of olefins to ketones.

2. DESCRIPTION OF THE PRIOR ART

U.S. Pat. No. 3,600,443 relates to a process for the oxidation of ethylene and propylene to the corresponding aldehyde or acid in the presence of oxygen and water vapor employing a vapor phase process in which the catalyst comprises a two-component heteropolyacid or oxide catalyst. The first component is an oxide of V, W or Mo, and the second component is an acid or oxide of B, Al, Si, Ti, Ge, Zr, Sn, Ce, P, As, Sb, Bi, S, Cr, Se, Te, Mn, Fe, Co or Ni. However, a significant selectivity loss to carbon dioxide and carbon monoxide was obtained in the preparation of acetone from propylene, and in the formation of acetaldehyde from ethylene. In the case of ethylene, increased conversion in a cerium-molybdenum-phosphomolybdic acid system was obtained at the expense of increased conversions to carbon oxides.

British Pat. No. 1,029,175 to Shell describes the vapor phase process in which olefin is reacted with oxygen at temperatures of less than 350° C. in the presence of water vapor an a halogen, using a supported Group VIII noble metal catalyst containing either an iron, cobalt, nickel, or Group I or VII transition metal compound optionally together with an alkali metal compound. Catalyst activity is stated to be further enhanced by additional use of one or more transition metal compounds of Groups III–VI, such as the rare earth metal compounds, with mixtures of lanthanum and neodymium being exemplified. The oxidation of propylene is indicated to give acetone as the main reaction product. Such a halide-containing catalyst system has severe disadvantages due to the corrosivity of halide-containing systems. In addition, the process of British Pat. No. 1,029,175 provides undesirably high selectivities to carbon dioxide by-product.

R. A. Acuna et al., *Anales de Quimica* 1978, supp. 1, pages 17–23, report a study of the partial oxidation of propylene in the absence of an oxygen gas feed and in the presence of steam at atmospheric pressure and at temperatures of from 200° to 400° C. over mixtures of various supported metal oxides containing molybdenum oxide together with oxides of tin, iron, bismuth or antimony in bimetallic catalysts, as well as various supported trimetallic catalysts containing oxides of molybdenum and iron and, as a third metal oxide, either an oxide of tin, neodymium, antimony, cobalt, bismuth, niobium or copper. Comparisons of propylene oxidation over a trimetallic oxide catalyst containing molybdenum, iron and neodymium showed a large selectivity loss to carbon monoxide and carbon dioxide, the total selectivity to these oxides ranging from about 48 to 87 percent at temperatures of from 300° to 380° C.

Other early patents to the conversion of olefins to product mixtures containing ketones are U.S. Pat. No. 2,523,686 and British Pat. No. 876,024.

U.S. Pat. No. 2,523,686 to W. F. Engel of Shell employs oxide catalysts containing (1) an oxide of a metal of Groups II, III, IV, or VI of the Periodic Table and (2) a metal or partially reduced oxide of a metal of Group IB, Group VII or Group VIII of the Periodic Table, and prepares saturated open-ended ketones from olefins of at least three carbon atoms per molecule in a vapor phase process in the presence of steam and under defined conditions. Dutch Pat. No. 59,179, also to W. F. Engel, relates to the similar catalyst systems. British Pat. No. 876,024 converts olefins into the corresponding aldehydes and ketones by passing a mixture of the olefin and oxygen, optionally with steam, over catalysts containing metal compounds whose cations and metals of a transition metal of the fifth to eighth group or first sub-group of the Periodic System and whose anions are derived from strong acids. Exemplified strong acid salts are those containing halide (Cl, Br), $NO_3^-$ and $PO_4^=$.

SUMMARY OF THE INVENTION

In one respect, an improved process is provided for forming ketones from the corresponding olefins in the vapor phase in the presence of water vapor employing a heterogeneous catalyst selected from the group consisting of Ce, Nd and La and compounds and complexes thereof, optionally containing at least one metal compound or complex selected from the group consisting of Group VIB metals and Group VIII noble metals, and mixtures thereof. It has been surprisingly found that these catalysts effect the formation of ketones in high selectivities with minimal selectivities to the undesirable carbon dioxide and carbon monoxide by-products. It has been further found that the catalysts of this invention effect the above results without the formation of substantial amounts of hydrogenation by-products, such as butane from butene feeds, and such olefin saturation products have been detected in the gaseous effluents from the process of this invention in only minimal amounts, if at all.

The process of this invention, in which the ketone is formed in an $O_2$-free reaction zone, also avoids the use of explosive $O_2$-olefin gas mixtures and therefore greatly minimizes the hazards and expense associated with the handling of such $O_2$-olefin gas mixtures.

It has been further found that the catalysts of this invention effect the above results without the formation of substantial amounts of hydrogenation by-products, such as butane from butene feeds, and such olefin saturation by-products have been detected in the gaseous effluents from the process of this invention in only minimal amounts, if at all.

In other respects, an improved process is provided for forming ketones in which molecular oxygen is also fed to the reaction zone. Surprisingly, use of the molecular oxygen containing feed still permits the formation of ketones in high selectivities with minimal selectivities to the undesirable carbon dioxide and carbon monoxide by-products.

DETAILED DESCRIPTION OF THE INVENTION

Catalyst

The catalysts of this invention comprise at least one member selected from the group consisting of Ce, Nd and La, preferably in a supported form. The catalyst metal can be present in a variety of forms including metallic Ce, Nd or La, a compound or complex thereof or a mixture thereof. When present as a compound, the catalyst metal can be chemically combined with an inorganic anion such as oxygen, sulfur and halide (F, Cl, Br or I). Preferred are non-halide catalysts such as selected from the group consisting of Ce, Ne and La oxides, sulfides and mixtures thereof. Particularly preferred are the oxides and sulfides such as $CeO_2$, $Ce_2O_3$, CeS, $Ce_2S_3$, $Ce_3S_4$, $Nd_2O_3$, NdS, $Nd_2S_3$, $La_2O_3$, LaS, $La_2S_3$, and $La_3S_4$.

The catalyst can optionally contain as a promoter a member selected from the group consisting of a metal or metal compound or complex of a Group VIB metal, a Group VIII noble metal or a mixture thereof. Thus, also suitable as catalyst for the vapor phase process of this invention are Ce, Nd and La catalysts containing, as the metal or as compounds or complexes thereof, any one of Cr, Mo, W, Ru, Rh, Pd, Os, Ir and Pt. These additional elemental components of the catalyst can be present as the metals themselves (that is, in the reduced state) or as compounds or complexes thereof, or as mixtures of the foregoing. Any of the inorganic anions discussed above with respect to Ce, Nd and La are also suitable as anions with which the additional Group VIB or Group VIII noble metals can be combined. As with the Ce, Nd and La component, the Group VIB and/or noble metal will be preferably present in the non-halide form, e.g., an oxide or sulfide. Illustrative of suitable bimetallic catalysts of this invention are Ce—Mo, Ce—W, Ce—Rh, Ce—Cr, Ce—Pd, Ce—Pt, Ce—Ir, Ce—Ru, Ce—Os, Nd—Mo, Nd—W, Nd—Rh, Nd—Cr, Nd—Pd, Nd—Pt, Nd—Ir, Nd—Ru, Nd—Os, La—Mo, La—W, La—Rh, La—Cr, La—Pd, La—Pt, La—Ir, La—Ru and La—Os oxides and sulfides, and mixtures of the foregoing. Illustrative trimetallic catalysts of this invention are oxides and sulfides of ce—Cr—Ru, Ce—Mo—Rh, Ce—W—Rh, Ce—Mo—Pd, Ce—Mo—Os, Ce—Mo—Pt, Ce—W—Pd, Ce—W—Os, Nd—Cr—Ru, Nd—Mo—Rh, Nd—W—Rh, Nd—Mo—Pd, Nd—Mo—Os, Nd—Mo—Pt, Nd—W—Pd, Nd—W—Os, La—Cr—Ru, La—Mo—Rh, La—W—Rh, La—Mo—Pd, La—Mo—Os, La—Mo—Pt, La—W—Pd, La—W—Os and mixtures of the foregoing. Especially preferred are oxides and sulfides of Rh—Ce—Mo, Ce—Mo, Rh—Nd—Mo, Nd—Mo, La—Rh—Mo and La—Mo. The selected Ce Nd or La catalyst metal is preferably present in the promoted catalysts of this invention in a total catalyst metal (Ce, Nd, and/or La):promoter metal weight:weight ratio of from about 0.0001:1 to 10:1, and more preferably from about 0.01:1 to 1:1. For example, a Ce—Mo catalyst will preferably contain from about 0.0001 to 10 parts by weight of Ce per part by weight of Mo, and more preferably from about 0.01 to 1 part by weight of Ce per part by weight of Mo. Similarly, in Nd—Rh—Mo catalysts, the weight ratio of Nd:(Rh+Mo) will preferably range from about 0.0001 to 10:1, and more preferably from about 0.01 to 1:1.

The catalysts which are used in the process of the present invention are solids which can be prepared by any of the methods known in the art. Furthermore, they can be employed in any suitable form, for examples as granules, pellets, powders and the like, and they can be either used as such or supported (as is preferred) on or admixed with an inert material, such as alumina, silica, silica-alumina, zeolites, pumice, any of the activated earths, kieselguhr, clays and the like. The preferred support for the catalyst of this invention is alumina, and most preferably gamma-alumina.

Preferred supported bimetallic catalysts of this invention are those containing from about 0.1 to 10 wt. % Ce, Nd or La together with from about 1 to 30 wt. % of a Group VIB metal (e.g., Mo or W), and more preferably those containing from about 1 to 5 wt. % Ce, Nd or La together with from about 3 to 15 wt. % of a Group VIB metal (e.g., Mo or W), calculated as wt. % of the indicated metals based on the total weight of the supported catalyst. Preferred supported trimetallic Ce, Nd or La catalysts of this invention are those containing (based on the total weight of the supported catalyst) from about 0.001 to 5 wt. % of a Group VIII noble metal (e.g., Rh, Pd, Pt or Ru), from about 0.1 to 10 wt. % Ce, Nd or La together with from about 1–30 wt. % Mo, and, more preferably, those containing from about 0.1—10 wt. % of a Group VIII noble metal (e.g., Rh, Pd, Pt or Ru), from about 1 to 5 wt. % Ce, Nd or La together with from about 3 to 15 wt. % of a Group VIB metal (e.g., Mo or W). Exemplary of preferred supported trimetallic catalysts of this invention are those containing (based on the total weight of the supported catalyst) from about 0.001 to 5 wt. % Rh, from about 0.1 to 10 wt. % Ce, Nd or La, and from about 1 to 30 wt. % Mo, and, more preferably, those containing from about 0.1 to 1.0 wt. % Rh, from about 1 to 5 wt. % Ce, Nd or La together with from about 3 to 15 wt. % Mo.

Most preferably, the catalyst composition ranges from 1 to 30 wt. % of catalyst metals in relation to the total weight of the supported catalyst.

The supports themselves are preferably characterized by a specific surface area of at least about 10 square meters per gram, and more preferably from about 25 to 200 square meters per gram (as determined by the BET method), and by a pore volume of at least about 0.1 cc./gm, and preferably from about 0.2 to 1.5 cc./gm (as determined by mercury porosimetry).

The catalysts can themselves be formed from a thermally decomposable salt so that a suitable solution of the selected cerium salt, for example, can then be impregnated on to the surface of a catalyst support followed by calcining at a temperature of at least about 400° C. for sufficient time to activate the catalyst. Generally, a time of from about 1 to 5 hours will be sufficient at a temperature within the range of 300° to 600° C. This calcining step can be conducted in the presence of air or $H_2S$ or an inert gases such as nitrogen, He and the like. The particularly decomposable compound selected will influence the anion associated with the Ce, Nd or La catalyst metal and promoter cation in the supported catalyst following the calcining step. Thus, a thio-salt of Ce, Nd or La catalyst metal and/or promoter, such as Ce, Nd or La thiomolybdates or ammonium thiomolybdates will be generally calcined to form the corresponding Ce, Nd or La sulfide catalyst. Non-thio salts, such as nitrate, carboxylates, carbonate and the like which do not contain S, will generally yield the corresponding Ce, Nd or La oxide catalyst on decomposition when the decomposable salt itself contains oxygen and when the calcining is conducted in an $O_2$-containing gas (e.g., air). Similarly, calcining the above S-free Ce, Nd or La and promoter salts in the presence of an $H_2S$, COS or $CS_2$ atmosphere will generally provide a catalyst containing the corresponding metal sulfides.

The selected catalyst components (e.g., Ce, Nd or La salts) such as the mono- or di-carboxylate of 1 to 10 carbon atoms (e.g., the acetate, oxalate, and the like) oxide, carbonate, nitrate and the like, alone or in combination with a selected promoter compound, e.g., ammonium paramolybdate) are intimately mixed in the presence of a solvent so as to produce a solution or a flowable paste. Then the selected support is impregnated with this liquid mixture and evaporation is carried out under the selected temperature conditions to obtain a dry solids. Water may be used as the solvent for mixing the catalyst components, but oxygenated organic compounds such as alcohols, ethers, esters, dioxane and the like can also be used.

A particularly preferred catalyst of this invention is prepared by first depositing (e.g., by vacuum impregnation) the selected support (e.g., gamma-alumina) with a thermally decomposable molybdenum compound (e.g., ammonium paramolybdate or thiomolybdate), followed by drying and calcining to form solids having molybdenum salts deposited thereon. Thereafter, the selected decomposable Ce, Nd or La compound (e.g., cerium nitrate) is deposited thereon, e.g., by vacuum impregnation, followed by a second drying and calcining of the solids. If desired, a Group VIII noble metal promoter compound (e.g., a rhodium salt such as rhodium nitrate) can then be deposited on the Mo—Ce/Nd/La catalyst, again followed by drying and calcining. Alternatively, the preferred catalyst can be prepared by depositing the selected Group VIII noble metal promoter compound prior to, or simultaneously with the deposition of the selected Ce, Nd or La compound onto the surface of the solids on which molybdenum has been previously deposited. Each drying step can be performed at temperatures within the range of from about 100° to 300° C. for a time sufficient to remove substantially all water (in the case of use of aqueous solutions of the foregoing metal salts) or at a temperature above the solvent boiling point to about 300° C. for removal of any other selected solvent used during the impregnation or deposition of the metals, optionally together with passing of an inert gas such as nitrogen over the solids' surface to facilitate the removal of the water or solvent. The calcining temperatures and times are as described above.

Formation of especially preferred supported Mo sulfide solids from thermally decomposable thiomolybdate compounds is more completely described in our co-pending application, Ser. No. 420,626, entitled "Improved Catalytic Process for the Oxidation of Olefins to Ketones", filed on even date herewith, whose disclosure is hereby incorporated by reference.

The supported catalyst thus prepared will generally have a surface area of at least about 5 m$^2$/gm (and preferably at least 40 M$^2$/gm) and can be used in a fixed bed and can also be used in a fluidized bed or other conventional means of housing the catalyst particles for ultimate contact with the gaseous reactants.

Olefin Conversion Process

The olefinic hydrocarbons which can be employed as reactants in the process of this invention are those which contain an aliphatic chain of at least two carbon atoms in which there exists at least one aliphatic double bond, —HC=CH—. Suitable olefinic hydrocarbons are those which are normally gaseous as well as those which are liquids at room temperatures but which can exist in the gaseous form at the elevated temperature and pressure conditions which are employed during the reaction. Representative olefinic reactants which can be employed, either alone or in combination, are propylene, 1-butene, 2-butene, 1-pentene, 2-pentene, 1-hexene, 2-hexene, 3-hexene, 3-methyl-1-pentene, cyclobutene, 1-heptene, 2-heptene, 1-octene, 2-octene, 1-nonene, 2-nonene, 1-decene, cyclohexene, cyclooctene, 1-dodecene, 1-hexadecene, allyl benzene, propenyl benzene, 3-phenyl-1-hexene, 4-o-tolyl-1-butene, and 1,6-diphenyl-3-hexene. Thus, suitable olefins include (1) linear mono olefins of 2 to 20 carbon atoms, inclusive of terminal olefins, i.e., olefins, having a terminal $H_2C$=CH-group, and internal olefins having the carbon-carbon double bond, as a —HC=CH— group in an internal carbon-carbon bond of the olefin, and (2) cyclic mono-olefins of 3 to 20 carbon atoms having a —HC=CH— group in the cyclic ring. Particularly suitable for this invention are linear alkenes having from 2 to 10 carbon atoms and cycloalkenes of 4 to 10 carbon atoms, and most preferred are alkenes having from 4 to 10 carbon atoms. Illustrative of these preferred classes of olefin feeds are those comprising 1-butene, 2-butene, 1-hexene, 1-pentene, propene, 1-octene, cyclohexene, cyclopentene, cyclobutene and the like, and mixtures thereof.

Paraffins (such as alkanes of 2 to 20 carbon atoms) and isoolefins (i.e., olefins having a >C=C< group in which one or both carbon atoms are hydrocarbyl substituted, such as 2-methyl-2-butene) can be also present in the gas feed to the oxidation zone in the practice of this invention, but they are essentially unreactive in forming the desired ketones.

Preferred olefinic feeds are olefin gas mixtures obtained from the refining of crude oil. Thus, butene cuts from such refineries typically contain n-butenes (1-butene and 2-butene) which will be converted by this process into 2-butanone, and also typically contain butane and isobutene.

The process of this invention is effected by passing the selected olefin and water vapor and (optionally) molecular oxygen over the surface of a catalyst of this invention under conditions such as to maintain a vaporous olefin in the reaction zone. The conditions of temperature and pressure under which this can be performed can vary widely depending on such factors as the particular olefin selected for use, the space velocity of gases through the reactor and other factors. Generally, however, a temperature of from about 125° to 600° C., preferably from about 200° to 400° C., will be entirely suitable. Most preferably, where the alkene comprises butene-1 or butene-2, the temperature within the catalyst reactor is maintained within the range of from about 250° to 375° C. Similarly, for cycloalkenes such as cyclohexene, a temperature in the range of from about 125° C. to about 200° C. is most preferable. The pressures are in no way critical and will generally range from about 0 to 2000 psig, preferably from about 5 to 150 psig, although higher or lower pressures are also suitable.

The space velocity of the total gases through the oxidation reactor are also not critical and can range from 100 to 10,000 v/v/hr., and preferably from about 200 to 6,000 v/v/hr., where "v" represents a unit of volume (e.g., "cc").

The reaction can be carried out either batchwise, continuously, or semi-continuously. In batch operations, the gaseous reactants may be placed, together with the catalyst, in a suitable pressure vessel and allowed to remain there under the desired reaction conditions for a suitable reaction interval, which will generally range from about 0.01 to 10 hours or more, depending on the degree of reaction completeness sought. In continuous operation, the gaseous reactants are passed through a body of the catalyst supported within a reactor vessel, which can be any of the conventional equipment employed by the industry for such reactions.

The water vapor (and $O_2$, where employed) can be combined and premixed with, or introduced separately from, the olefin feed, or they can be passed to the reaction vessel via separate conduits. The manner of contacting the water vapor and olefin is not critical and any of the conventional gas-gas contacting methods employed in the industry may be used.

The ratio of olefin:water vapor can also vary widely. Generally, the molar ratio of olefin:water vapor introduced to the reactor will range from about 2:1 to 1:20, preferably from about 1:1 to 1:10. Where $O_2$ is employed, the olefin:oxygen molar ratio in the total gases fed to the reactor will generally range from about 0.5:1 to 10:1, and more typically from about 1:1 to 5:1. However, ratios outside the foregoing ranges can also be employed.

An inert gaseous diluent such as nitrogen or paraffin can also be introduced together with the other gaseous feeds to the reactor in order to achieve a desired high space velocity and to minimize hot spots which could result in an over-oxidation of the feed and/or reactants during the exothermic ketone formation using an $O_2$-containing feed.

Preferably, the olefin, water vapor and $O_2$ (where employed) are contacted with a non-halide catalyst of this invention and in the substantial absence of free halide (that is a molar ratio of free halide:olefin of less than about $1 \times 10^{-5}:1$) in order to minimize corrosion difficulties.

The ketones which are formed will depend, of course, on the particular olefin(s) employed in the feed. Thus, use of alkene as the olefin will result in forming the corresponding alkanone having the same number of carbon atoms as the alkene fed (acetone from propylene; methyl ethyl ketone from 1-butene, 2-butene or mixtures thereof; cyclohexanone from cyclohexene). The process is particularly suitable for forming alkanones having from 4 to 10 carbon atoms.

The major alcohol product formed in the process of this invention will correspond to the carbon skeleton of the ketone product, e.g., secondary butyl alcohol corresponding to methyl ethyl ketone.

The ketones and alcohols produced by the process of this invention can be recovered from the reaction mixture in any desired manner, such as by distillation or by extraction with water or other solvents followed by distillation. Preferably, at least a portion of the unreacted gases are recovered and recycled to the reactor in addition to fresh feed gases in order to maximize olefin conversion. Alternatively, a series of reactor vessels can be employed and the unreacted gases from the first vessel can then be passed as feed to the second vessel, together with make-up gaseous olefin and water vapor as required.

Gaseous $H_2$, which is also formed in the overall reaction, illustrated by equation (I) below, can be readily recovered from the reaction effluents.

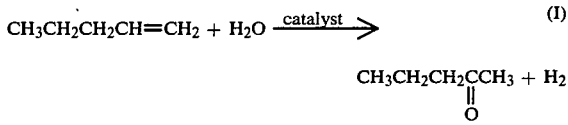

$$CH_3CH_2CH_2CH=CH_2 + H_2O \xrightarrow{catalyst} \tag{I}$$
$$CH_3CH_2CH_2\underset{\underset{O}{\|}}{C}CH_3 + H_2$$

Molecular oxygen is an optional, additional component of the feed to the reaction zone for conversion of the olefin to the desired ketone. When employed, the olefin:oxygen molar ratio in the total gases fed to the reactor will generally range from about 0.5:1 to 10:1, and more typically from about 1:1 to 5:1. However, ratios outside the foregoing ranges can also be employed.

However, the reaction zone, in which the desired reaction between the olefin and water vapor to form the selected ketone is effected, is preferably oxygen-free, that is, contains a molar ratio of added molecular oxygen to olefin of less than about 0.01:1. Molecular oxygen, therefore, is not a required component of the gas feed to the process and its presence serves to increase the amount of oxygenated by-products, including carbon dioxide and carbon monoxide, as will be illustrated in the examples which follow.

The choice of whether or not to employ $O_2$ in the gas feed to the reaction may be made based on a variety of process parameters. The $O_2$-containing feeds will yield a more exothermic reaction, and hence provide an opportunity for higher level heat recovery from the reaction effluent. On the other hand, use of $O_2$ in the feed generally results in an increase in the amount of undesired by-products which are made, such as CO and $CO_2$, although olefin conversions are somewhat increased over comparative reactions in which $O_2$ is excluded from the reaction zone. Of course, the precise balance of these potential benefits and disadvantages of $O_2$-containing feeds must be made on a case-by-case basis.

While not wishing to be limited thereby, it is believed that the ketone product formed by the process of this invention proceeds by way of an alcohol intermediate corresponding to the skeleton structure of the ketone product. It is believed that this is the explanation for the quantity of alcohol product which is also formed and detected in the examples that follow. For example, butene is converted to a mixture of ketone and secondary butyl alcohol. Accordingly, our invention also provides a process for contacting such an alcohol with water vapor and $O_2$ (when employed) in the presence of a catalyst of this invention to form a corresponding ketone. Process parameters including feed ratios, reaction times, space velocities, temperatures, pressures and the like, which are discussed above for the use of olefin-containing feeds, are also useful in the embodiment of this invention in which the alcohol is employed as the feed. The molar ratio of alcohol:water vapor is generally from about 0.01:1 to 100:1, and preferably from about 0.1:1 to 10:1, and the alcohol:oxygen molar ratio (when O₂ is employed) will generally be from about 0.1:1 to 100:1, preferably 1:1 to 10:1. Alcohols which are suitable as feeds correspond to any of the above-discussed product alcohols of this invention. Therefore, particularly suitable are alkanols, and especially secondary alkanols, having from 3 to 10 carbon atoms per molecule. The utility of the catalysts of this invention for conversion of alcohols to ketones can be readily seen from the following examples, and it will also be apparent to one skilled in the art that recycle of recovered alcohol by-product to an olefin-reaction zone using a catalyst of this invention will provide improved overall utilization of an olefin-containing feed as a result of the further reaction of the thus-recycled alcohol by-product.

The process of this invention can be further illustrated by reference to the following examples wherein percent conversions and selectivities are mole percent.

Product selectivities in the examples were determined by gas chromatographic analysis after steady-state conditions were observed. Products formed were methyl ethyl ketone, CO, $CO_2$, secondary butyl alcohol, butyl mercaptan and the balance unknowns. In the examples, the gaseous effluents from the reactor were analyzed for butene consumed, using isobutane as a standard and employing response factors determined for the GC by calibration with a known gas mixture.

EXAMPLE 1

Gamma-alumina (30 cc; 12–20 mesh; 100 m²/gm; 0.43 cc/gm pore volume; Alfa Products) were dried in air in a Linberg furnace at 500° C. for 3 hours to give a dry weight of 24.6 grams. Ammonium heptamolybdate [$(NH_4)_6Mo_7O_{24}.4H_2O$] (4.23 grams) was dissolved in distilled water to make a 11.0 cc. solution and transferred into a 60 cc. dropping funnel. The catalyst support was placed in a 125 cc. glass filtering flask equipped with side arm for pulling a vacuum, and the filtering flask was attached to the dropping funnel using a rubber stopper. After evacuation (to a pressure of −15 in Hg) of the air trapped inside the catalyst support via the vacuum line, the ammonium heptamolybdate solution was added dropwise to the catalyst support to achieve complete wetness. The impregnated wet catalyst was placed in a stainless steel gauze boat and dried in air at 125° C. for 1 hour, 250° C. for 1 hour, and 350° C. for 1 hour, and finally calcined by raising the furnace temperature to 500° C. (at a rate of about 10° C./min.), which was maintained for 3 hours. After cooling, one half of the solids were again impregnated using the above procedure with a 5.5 cc. distilled water solution containing 1.63 grams of cerium trinitrate. After the drying and calining procedure was repeated, the resulting catalyst was found to comprise cerium oxide-molybdenum oxide on gamma-alumina and to contain 3.7 wt. % Ce and 9.5 wt. % Mo, calculated as the respective metals, based on the weight of the catalyst support.

Ten cc. of the Ce—Mo oxide catalyst and 20 cc. of fused ceramic inert (12–20 mesh) were well mixed and loaded into a test reactor which comprised a 24 inch (0.38 inch ID) stainless steel tubular reactor equipped with gas inlet and gas outlet at opposing ends of the tubular reactor. The reactor was then heated to a temperature of 304° C. (which was maintained by means of an electric heating tape and a Gardsman temperature control. Temperatures in the reactor were determined by means of a thermocouple positioned in the center of the catalyst bed. A gaseous mixture containing butene-1, oxygen, nitrogen and water vapor was then passed as feed to the reactor at a gas hourly space velocity of 6,336 with the oxygen and nitrogen being employed as a 1:9 volume:volume mixture of oxygen and nitrogen. The feed rates for these gaseous components at the reaction temperature were 102 cc. per minute of butene-1, 730 cc. per minute of the oxygen/nitrogen mixture and 224 cc. per minute of water vapor. A gaseous inlet pressure of 6.4 psig was employed throughout the reaction. The gas mixture was continuously withdrawn from the reactor and sampled and analyzed by means of an on-line gas chromatograph. After achieving steady state conditions, butene conversion was found to be 21.8% and a selectivity to methyl ethyl ketone of 66.2% was obtained. Also formed was secondary butyl alcohol in a selectivity of 7.6% and CO in a selectivity of 1.5%. The total run time for this experiment was 10.8 hours.

EXAMPLE 2

The catalyst used in Example 1 was contacted in a separate run under the same conditions except that the gaseous feed to the reactor was 60 cc. per minute of butene-1, 730 cc. per minute of the oxygen-nitrogen gas mixture and 224 cc. per minute of water vapor. This provided a gas hourly space velocity of 6,084 cc/cc/hr. A temperature of 292° C. was maintained throughout the run (12.5 hours). After achieving steady state conditions, methyl ethyl ketone was found to be formed in a selectivity of 69.4% at a 3.8% butene conversion. Secondary butyl alcohol was found to be formed in the selectivity of 25.8%. No CO or $CO_2$ was detected as a by-product.

EXAMPLE 3 FOR COMPARISON

To illustrate the advantages achieved by use of the cerium-molybdenum catalysts of Examples 1–2, a series of runs were conducted employing molybdenum oxide catalyst in the absence of Ce. Following the procedure of Example 1, 45 cc. of gamma-alumina (12–20 mesh; Alfa Products) was dried in air at 250° C. for 2 hours. Thereafter, 6.5 grams of ammonium paramolybdate [$(NH_4)_6Mo_7O_{24}.4H_2O$] was dissolved in distilled water to make a 18.0 cc. solution. The resulting solution was employed in vacuum impregnation of the dried gamma-alumina solids (37.1 gms) using the procedure of Example 1. After the vacuum impregnation, the wet solids were dried in air at a temperature of 125° C. for 1 hour and a temperature of 250° C. for 1 hour, followed by 350° C. for 1 hour, and then calcined in nitrogen at 500° C. for 3 hours. The catalyst was found to comprise molybdenum oxides on gamma-alumina, which could be represented by the formula: $MoO_3$. The catalyst loading was found to be 9.5% of molybdenum, calculated as the element, based on the total weight of the catalyst support.

Ten cc. of the supported catalyst was then charged to the reactor after mixing the catalyst with 20 cc. of fused ceramic inert (12–20 mesh). This oxide catalyst was employed in two runs under the conditions of temperature and feed rates summarized in Table I, yielding the data set forth in that Table. For convenience, Table I also repeats the data of Examples 1 and 2).

Thus, the Ce—Mo oxide catalysts of Examples 1 and 2 provided high MEK and SBA product selectivities and minimal selectivity loss to by-product $CO_2$ and CO.

TABLE I

| | Run No. | Time (hrs) | Temp. (°C.) | Press. psig | Gas Feed (cc/min.) | | | GHSV (cc/cc hr.) (2) | Butene Conv. (%) | % Selectivities to: | | | | Total Product (MEK + SBA) | Total $CO_2$ + CO |
|---|---|---|---|---|---|---|---|---|---|---|---|---|---|---|---|
| | | | | | Butene | $H_2O$ Vapor | $O_2$ | | | MEK (3) | $CO_2$ | CO | SBA (4) | | |
| Compar. Ex. 3 | 1 | 2.0 | 300 | 7.1 | 60 | 224 | 730 | 6084 | 9.0 | 80.6 | 6.9 | 2.8 | 8.1 | 88.7 | 9.7 |
| | 2 | 5.0 | 305 | 7.1 | 102 | 224 | 730 | 6338 | 20.3 | 77.0 | 3.8 | 1.9 | 4.2 | 75.2 | 5.7 |
| Example | 1 | 10.8 | 304 | 6.4 | 102 | 730 | 730 | 6336 | 21.8 | 66.2 | 0 | 1.5 | 7.6 | 73.8 | 1.5 |
| Example | 2 | 12.5 | 292 | 6.4 | 60 | 730 | 730 | 6084 | 3.8 | 69.4 | 0 | 0 | 25.8 | 95.2 | 0 |

(1) $O_2$ feed = (10 vol. % $O_2$, 90 vol.% $N_2$ gas mixture).
(2) Total gas hourly space velocity.
(3) Methyl ethyl ketone.
(4) Secondary butyl alcohol.

EXAMPLE 4

The cerium-molybdenum oxide catalyst used in Example 2 was sulfided in the reactor by contacting the oxide catalyst with a mixture of hydrogen sulfide gas (190 cc./min.; charged as 6 vol. % $H_2S$ in $N_2$) and $H_2$ (230 cc./min.) at a temperature of 325° C. and a pressure of 9.0 psig for 3 hours followed by $H_2$ gas stripping (520 cc./min.) at the same temperature and pressure for 1 hour to remove any absorbed, unreacted $H_2S$. The resulting catalyst was then determined to comprise cerium and molybdenum sulfides and to contain 3.7 wt. % Ce and 9.7 wt. % Mo, calculated as the respective elements, based on the weight of the catalyst support.

The Ce—Mo sulfide catalyst was then contacted with a butene feed having the composition employed in Example 1 using the procedure and conditions of that Example, except that a reaction temperature of 307° C. and a gas inlet pressure of 9.1 psig was used during the run (3 hours). After achieving equilibrium conditions, methyl ethyl ketone was found to have been formed in a selectivity of 86.1% at a butene conversion of 5.6%. Secondary butyl alcohol was formed in 3.5% selectivity, and butyl mercaptan selectivity was 4.7%. No CO or $CO_2$ were detected as by-products.

EXAMPLE 5

The butene oxidation procedure of Example 4 was repeated employing the cerium-molybdenum sulfide catalyst used in that Example, except that the gas feed to the reactor comprised 60 cc. per minute of butene-1, 730 cc. per minute of the oxygen:nitrogen mixture and 224 cc. per minute of water vapor, thereby using a gas hourly space velocity of 6,084 cc/cc/hr. A reaction temperature of 303° C. and a gas inlet pressure of 9.1 psig was used during the run (5.3 hours). Methyl ethyl ketone selectivity was 87.4% at a butene conversion of 6.8%. Secondary butyl alcohol selectivity was 4.7% and butyl mercaptan selectivity was zero. Again, no selectivity loss to CO or $CO_2$ was found.

EXAMPLE 6

The butene oxidation procedure of Example 4 was again repeated, using the Ce—Mo sulfide catalyst employed in Example 5, except that the gas feed to the reactor comprised 60 cc./min. of butene-1, 380 cc./min. of $O_2$:$N_2$ and 224 cc./min. of water vapor, giving a gas hourly space velocity of 3,984 cc/cc/hr. A reaction temperature of 306° C. and a gas inlet pressure of 9.1 psig was used during the run (6.4 hours). Methyl ethyl ketone selectivity was 88.7% at a conversion of 3.9%. No selectivity loss to CO or $CO_2$ was observed and secondary butyl alcohol and butyl mercaptan selectivities were found to be 8.6% and 1.7% respectively.

EXAMPLE 7 FOR COMPARISON

To illustrate the advantages achieved by use of the Ce—Mo sulfide catalysts of Examples 4–6, the Mo oxide catalyst of Comparative Example 3 was sulfided by contacting the oxide catalyst in the reactor with a mixture of hydrogen sulfide gas (charged at a rate of 190 cc./min. as 6 vol. % $H_2S$ in $N_2$) and hydrogen gas (230 cc./min.) at a reactor temperature of 320° C. and a gas inlet pressure of about 7.1 psig, for a period of 3 hours. Gaseous $H_2$ (520 cc./min.) was then passed through the reactor for 1 hour at the same temperature and gas inlet pressure to remove any absorbed, unreacted $H_2S$.

Thereafter, a butene-containing feed was introduced to the reactor in two runs employing the conditions and providing results as indicated in Table II, which also summarizes the results of Examples 4–6, for convenience.

The Ce—Mo sulfide catalysts of Examples 4–6 provided significantly increased selectivities to ketone and total (ketone+alcohol) product, and formed no detectable levels of the undesirable $CO_2$ or CO by-products, in contrast to the much higher selectivity loss to these by-products and the lower ketone and total product selectivities with the Mo sulfide catalyst alone.

TABLE II

| | Run No. | Time (hrs) | Temp. (°C.) | Press. psig | Gas Feed (cc/min.) | | | GHSV (cc/cc hr.) (2) | Butene Conv. (%) | % Selectivities to: | | | | | Total Product (MEK + SBA) | Run $CO_2$ + CO |
|---|---|---|---|---|---|---|---|---|---|---|---|---|---|---|---|---|
| | | | | | 1-Butene | $H_2O$ Vapor | $O_2$ | | | MEK (3) | $CO_2$ | CO | SBA (4) | $C_4SH$ (5) | | |
| Compar. Ex. 7 | 1 | 5.0 | 305 | 7.1 | 60 | 224 | 730 | 6084 | 15.1 | 62.6 | 10.0 | 2.0 | 13.6 | 0.9 | 76.2 | 12.0 |
| | 2 | 5.8 | 298 | 7.1 | 102 | 224 | 730 | 6338 | 12.6 | 68.8 | 5.8 | 1.9 | 9.6 | 0.9 | 78.4 | 7.7 |
| Example | 4 | 3.0 | 307 | 9.1 | 102 | 224 | 730 | 6336 | 5.6 | 86.1 | 0 | 0 | 3.5 | 4.7 | 89.6 | 0 |
| Example | 5 | 5.3 | 303 | 9.1 | 60 | 224 | 730 | 6084 | 6.8 | 87.4 | 0 | 0 | 4.7 | 0 | 92.1 | 0 |

TABLE II-continued

| Run No. | Time (hrs) | Temp. (°C.) | Press. psig | Gas Feed (cc/min.) 1-Butene | Gas Feed (cc/min.) H2O Vapor | Gas Feed (cc/min.) O2 | GHSV (cc/cc hr.) (2) | Butene Conv. (%) | % Selectivities to: MEK (3) | % Selectivities to: CO2 | % Selectivities to: CO | % Selectivities to: SBA (4) | % Selectivities to: C4SH (5) | Total Product (MEK + SBA) | Run CO2 + CO |
|---|---|---|---|---|---|---|---|---|---|---|---|---|---|---|---|
| Example 6 | 6.4 | 306 | 9.1 | 60 | 224 | 730 | 3984 | 3.9 | 88.7 | 0 | 0 | 8.6 | 1.7 | 87.3 | 0 |

(1) O2 feed = (10 vol. % O2, 90 vol. % N2 gas mixture).
(2) Total gas hourly space velocity.
(3) Methyl ethyl ketone.
(4) Secondary butyl alcohol.
(5) Butyl mercaptan.

EXAMPLE 8

Using the procedure of Example 1, 30 cc. of the gamma-alumina were dried at 500° C. in air for 3 hours to give a dry weight of 27.2 gms and then vacuum impregnated, successively, with aqueous solution containing $(NH_4)_2Mo_7O_{24}$, $Rh(NO_3)_2$ and $Ce(NO_3)_3$. The first impregnation employed 10.6 cc. of an aqueous solution containing 4.77 gms of $(NH_4)_6Mo_7O_{24}.4H_2O$ in distilled water, and the impregnated-catalyst was dried in air at 125° C. for 1 hour, 250° C. for 1 hour and 350° C. for 1 hour, and then calcined in air at 500° C. for 3 hours. A 14.4 gram portion of the Mo impregnated, dried solids was then impregnated with the Ce salt using 5.2 cc. of an aqueous solution containing 1.72 gms of $Ce(NO_3)_3.6H_2O$ dissolved therein, once again followed by drying and calcining under the above four-step process. Finally, the solids were impregnated with the $Rh(NO_3)_3$ using 5.3 cc. of an aqueous solution containing 0.41 gm. of dissolved $Rh(NO_3)_3.2H_2O$, again followed by the above four-step drying and the calcining process. The resulting supported Ce—Rh—Mo oxide catalysts was found to contain 1.0 wt. % Rh, 3.7 wt. % Ce and 9.5 wt. % Mo, calculated as the metals, based on the weight of the total catalyst support.

Using the procedure of Example 1, 10 cc. of the Ce—Rh—Mo oxide catalyst was placed in the test reactor with 20 cc. of 12-20 mesh fused ceramic inerts and a gas feed comprising 60 cc./min. of a gas mixture containing 85 vol. % 1-butene, and 15 vol. % iso-butane, 380 cc./min. of $O_2:N_2$ (10:90 vol:vol) gas mixture and 224 cc./min. of water vapor was passed to the reactor (GHSV=3,874 cc/cc/hr.) using a reactor temperature of 305° C. and a gas inlet pressure of about 9.7 psig for 0.5 hour.

At a butene conversion of 12.4% the following selectivities were found: 67.0% methyl ethyl ketone, 25.0% $CO_2$ and 18% CO.

EXAMPLE 9 FOR COMPARISON

To illustrate the improved results obtained with the Ce—Rh—Mo oxide catalyst of Example 8, the catalyst preparation procedure of Example 8 was repeated, except that no $Ce(NO_3)_3$ was impregnated onto the gamma-alumina which was only subjected to the impregnation/drying/calcining of the salt thereon. Ten cc. of the resulting Mo-Rh oxide catalyst (containing 1.0 wt. % Rh and 9.5 wt. % Mo, calculated as the metals) was mixed with 20 cc. of the 12-20 mesh fused ceramic inerts and a series of runs were made using the conditions indicated in Table III below were performed.

Comparing Example 8 (conducted at 291° C.) and Run 9B (301° C.), the two closest reaction conditions, it is seen that the Rh—Mo oxide catalyst of Run 9-B provided an inferior MEK selectivity (43.8% vs. 67.0%, for the Ce—Mo—Rh oxide catalyst of Example 8) in addition to an increased selectivity loss to CO and $CO_2$ (39.1% vs. 26.8% for the Ce—Mo—Rh oxide catalyst of Example 8).

EXAMPLE 10

Following the $H_2S$ sulfiding/$H_2$ stripping procedure of Example 4, the Ce—Rh—Mo oxide catalyst of Example 8 was sulfided in the reactor and the resulting Ce-Rh-Mo sulfide catalyst was contacted with a gas feed containing 60 cc./min. of a gas mixture containing 85 vol. % 1-butene and 15 vol. % iso-butane, 380 cc./min. of $O_2:N_2$ (10:90 vol:vol) gas mixture and 224 cc./min. of water vapor (GHSV=3,984 cc/cc/hr.) at a temperature of 302° C. and a gas inlet pressure of 9.7 psig, for 1.5 hours.

At a butene conversion of 16.0%, the following selectivities were observed: 69.7% MEK, 1.8% SBA, 19.3% $CO_2$, 2.4% CO and 0.7% butyl mercaptan.

TABLE III

| | Run No. | Time (hrs) | Temp. (°C.) | Press. psig | Gas Feed (cc/min.) Butene (1) | Gas Feed (cc/min.) O2/N2 (2) | Gas Feed (cc/min.) H2O | GHSV (3) | Butene Conv. (%) | % Selectivity MEK (4) | % Selectivity CO2 | % Selectivity CO | % Selectivity SBA (5) |
|---|---|---|---|---|---|---|---|---|---|---|---|---|---|
| Compar. Ex. 9 | A | 8.9 | 250 | 7.1 | 102 | 730 | 224 | 6338 | 8.0 | 48.7 | 29.7 | 7.8 | .8 |
| Compar. Ex. 9 | B | 0.6 | 301 | 7.1 | 60 | 730 | 224 | 6084 | 29.4 | 43.8 | 20.9 | 18.2 | 2.5 |
| Compar. Ex. 9 | C | 5.9 | 312 | 7.1 | 102 | 730 | 224 | 6338 | 28.4 | 69.5 | 13.7 | 6.8 | 3.6 |
| Example 8 | | 0.5 | 291 | 9.7 | 60 | 380 | 224 | 3984 | 12.3 | 67.0 | 25.0 | 1.8 | 0 |

(1) Butene feed = 100% butene-1, in Comp. Ex. 9 Butene feed = 85 vol. % 1-butene, 15 vol. % iso-butane in Ex. 8.
(2) Total gas hourly space velocity (cc/cc/hr.)
(3) MEK = methyl ethyl ketone.
(4) SBA = secondary butyl alcohol.

EXAMPLE 11 FOR COMPARISON

The Rh—Mo oxide catalyst used in Comparative Example 9 was sulfided in the reactor using the procedure of Example 4 and the resulting Rh—Mo sulfide catalyst was tested for its butene oxidation activity. The run conditions and data obtained are summarized below in Table IV.

Under no conditions in Runs 11A-11C were the high MEK selectivities and low CO+$CO_2$ selectivities observed in Example 10 achieved. At the closest conditions, the Ce—Rh—Mo sulfide catalyst of Example 10 had over a 21 percentage points advantage in MEK selectivity (69.7% vs. 48.5% for Run 11-A) and formed over 15 percentage points less in $CO+CO_2$ selectivity loss ($CO+CO_2$ selectivities = 21.7% for Example 10 vs. 36.8% for the Rh—Mo sulfide catalyst of Run 11-A).

which these oxides of carbon were formed in large amounts as by-product. The example also illustrates the ability of this invention to employ a temperature of reaction in excess of a level at which carbon dioxide and CO begin to be formed when using a gas feed containing molecular oxygen.

TABLE IV

| | Run No. | Time (hrs) | Temp. (°C.) | Press. psig | Gas Feed (cc/min.) | | | | Butene Conv. (%) | % Selectivity | | | | |
|---|---|---|---|---|---|---|---|---|---|---|---|---|---|---|
| | | | | | Butene (1) | $O_2N_2$ (2) | $H_2O$ | GHSV (3) | | MEK (4) | $CO_2$ | CO | SBA (5) | $C_4SH$ (6) |
| Compar. Ex. 11 | A | 0 | 300 | 7.1 | 31 | 380 | 112 | 3138 | 36.3 | 48.5 | 31.5 | 5.3 | 0 | 0 |
| | B | 6.4 | 302 | 7.1 | 102 | 730 | 224 | 6338 | 18.4 | 48.1 | 26.2 | 8.5 | 0 | 0 |
| | C | 2.4 | 310 | 7.1 | 60 | 730 | 224 | 6084 | 46.9 | 58.6 | 12.7 | 6.2 | 0 | 0 |
| Example | 10 | 1.5 | 309 | 9.7 | 60 | 380 | 224 | 3984 | 16.0 | 69.7 | 19.3 | 2.4 | 1.8 | 0.7 |

(1) Butene feed = 100% butene-1, in Comp. Ex. 11 Butene feed = 85 vol. % butene-1, 15 vol. % iso-butane in Ex. 10.
(2) 10% $O_2$ in $N_2$.
(3) Total gas hourly space velocity (cc/cc/hr.).
(4) MEK = methyl ethyl ketone.
(5) SBA = secondary butyl alcohol.
(6) $C_4SH$ = butyl mercaptan.

EXAMPLE 12

The cerium-rhodium-molybdenum sulfide catalyst employed in Example 10 was tested in a separate run using the same procedure, except that the reaction temperature was 378° C. and the gas inlet pressure was 9.2 psig. The gas feed to the reactor comprised 60 cc/min. of a 85 vol. % 1-butene and 15 vol. % iso-butane gas mixture, together with 224 cc/min. water vapor and 380 cc/min. gaseous nitrogen, to provide a total gas hourly space velocity of 3,984 cc/cc/hr. No molecular oxygen was fed to the reactor. At a butene conversion of 3.3%, the following selectivities were observed: 97.5% methyl ethyl ketone, 1.4% secondary butyl alcohol and 1.1% butyl mercaptan. No CO or $CO_2$ by-products were detected. The total run time was 6.8 hours.

EXAMPLE 13

The butene conversion procedure of Example 12 was repeated employing 378° C. reaction temperature and a gas inlet pressure of 9.2 psig. In this run, the gas feed to the reactor comprised 104 cc/min. of the butene-1/isobutane gas mixture of Example 12, 224 cc/min. of water vapor and 730 cc/min. of gaseous nitrogen, to provide a total gas hourly space velocity of 6,336 cc/cc/hr. At a butene conversion of 1.3%, the following selectivities were observed: 97.3% methyl ethyl ketone, 2.0% secondary butyl alcohol and 0.7% butyl mercaptan. Again, no CO or $CO_2$ by-products were detected. The total run time was 9.9 hours.

As is seen from Examples 12 and 13, the ketone product was formed in a selectivity of about 97% in the absence of molecular oxygen. In addition, the alcohol product was formed in a selectivity of from about 1.4 to 2% at a temperature of 378° C. Since the catalyst comprised a sulfide catalyst of this invention, the oxygen molecules incorporated into the ketone and alcohol products are believed to have been derived from the water vapor introduced with the gas feed. Surprisingly, no detectable amounts of carbon dioxide or carbon monoxide were formed as by-products, thereby removing the significant disadvantage of prior art methods in

EXAMPLE 14

The procedure of Example 13 was repeated employing the cerium-rhodium-molybdenum catalyst used in Example 13, except that the nitrogen gas was also omitted from the gas feed to the test reactor. In this experiment, a temperature of 374° C. and a gas inlet pressure of 8.1 psig was employed at a total gas hourly space velocity of 1,704 cc/cc/hr., using a gas feed comprising 60 cc/min. of a gas mixture containing 85 vol. % 1-butene and 15 vol. % isobutane and 224 cc/min. of water vapor for 11.5 hours. At a butene conversion of 3.0%, product selectivity to a methyl ethyl ketone was observed to be 97.1% and secondary butyl alcohol selectivity was found to be 2.2%. In addition, butyl mercaptan was formed in an amount of 0.7%. No detectable amounts of carbon dioxide or carbon monoxide were found as by-product.

EXAMPLE 15

Using the procedure of Example 1, 15 cc. of the gamma-alumina (12–20 mesh) was dried in air at 500° C. for 3 hours to provide a dry weight of 13.84 grams. These solids were then impregnated with 5.3 cc. of an aqueous solution containing 4.08 grams of $Ce(NO_3)_3.6H_2O$, followed by drying at 125° C. for 1 hour, 250° C. for 1 hour, and 350° C. for 1 hour in air, and then by calcining at 500° C. for 3.8 hours, also in air. The oxide catalyst was found to contain 9.5 wt. % cerium, calculated as the element, based on the weight of the catalyst support.

Ten cc. of this oxide catalyst was then mixed with 20 cc. of fused ceramic inert (12–20 mesh) and then tested as in Example 1 in two runs, employing a gas feed to the reactor comprising 60 cc/min. of a butene-1 gas mixture (containing 85 vol. % butene-1 and 15 vol. % isobutane), 224 cc/min. water vapor and either 380 cc/min. of an oxygen-containing gas (10:90 vol:vol oxygen:nitrogen gas mixture) (Run 1) or 380 cc/min. of $N_2$ (Run 2) to provide a total gas hourly space velocity of 3984 cc/cc/hr. The data thereby obtained are set forth in Table V below.

TABLE V

| Run No. | Time (hrs) | Temp. (°C) | Press. psig | Gas Feed (cc/min.) Butene (1) | O₂ | N₂ | Water Vapor | GHSV (2) | Butene Conv. (%) | % Selectivities MEK (3) | CO₂ | CO | SBA (4) |
| --- | --- | --- | --- | --- | --- | --- | --- | --- | --- | --- | --- | --- | --- |
| 1 | 1.0 | 302 | 9.4 | 60 | 38 | 302 | 224 | 3984 | 0.6 | 32.5 | 38.5 | 0 | 14.6 |
| 2 | 3.0 | 366 | 9.4 | 60 | 0 | 380 | 224 | 3984 | 0.3 | 85.9 | 0 | 0 | 14.1 |

(1) Feed = 85 vol. % butene-1; 15 vol. % iso-butane.
(2) Total gas hourly space velocity, cc/cc/hr.
(3) Methyl ethyl ketone.
(4) Secondary butyl alcohol.

EXAMPLE 16

Gamma-alumina (30 cc; 12-20 mesh, 100 m²/gm. surface area; 0.45 cc/gm. pore volume; Alfa Products) was dried in air in a Linberg furnace to 500° C. for 3 hours to give a dry weight of 24.61 grams. Ammonium heptamolybdate [(NH₄)₆Mo₇O₂₄.4H₂O] (4.27 grams) was dissolved in distilled water to make a 11.0 cc solution which was transferred into a 60 cc dropping funnel. The catalyst support was placed in an 125 cc filtering flask equipped with a side arm for pulling a vacuum, and the filtering flask was attached to the dropping funnel using a rubber stopper. After evacuation (to a pressure of −15 in Hg) of the air trapped inside the catalyst support via the vacuum line, the ammonium heptamolybdate solution was added dropwise to the catalyst support to achieve complete wetness. The impregnated wet catalyst was placed in a stainless steel gauze boat and dried in air at 125° C. for 1 hour, 250° C. for 1 hour, and 350° C. for 1 hour, and finally calcined by raising the furnace temperature to 500° C. (at a rate of about 10° C./min.), which was maintained for 3 hours. After cooling, one-half of the solids were again impregnated using a 5.0 cc distilled water solution containing 1.46 grams of neodymium trinitrate using the above procedure. After the drying and calcining procedure was repeated, the resulting catalyst was found to comprise neodymium oxide-molybdenum oxide on gamma-alumina and to contain 3.7 wt. % Nd and 9.5 wt. % Mo, calculated as the respective metals, based on the catalyst support.

Ten cc. of the foregoing catalyst and 20.0 cc. of fused ceramic inert (12-20 mesh) were well mixed and loaded into a test reactor which comprised a 24 inch (0.38 inch-ID) stainless steel tubular reactor equipped with gas inlet and gas outlet at opposing ends of the tubular reactor. The reactor was then heated to a temperature of 295° C. (which was maintained by means of an electric heating tape and a Gardsman temperature control). Temperatures in the reactor were determined by use of a thermocouple positioned in the center of the catalyst bed. A gaseous mixture containing 1-butene, oxygen, nitrogen, and water vapor was passed to the reactor at a gas hourly space velocity of 3,984 cc/cc/hr., the oxygen and nitrogen being employed as a 10:90 volume:-volume mixture of oxygen and nitrogen. The feed rates for these gaseous components at the reaction temperature were 60 cc. per minute of butene-1, 380 cc. per minute of the oxygen/nitrogen mixture and 224 cc. per minute of water vapor. A gaseous inlet pressure of 9 psig was employed throughout the reaction. A gaseous effluent was continuously withdrawn from the reactor and was sampled and analyzed by means of an on-line gas chromatograph. After achieving steady state conditions, butene-1 conversion was found to be 6.9% and a selectivity to methyl ethyl ketone of 94% was obtained. Also formed was secondary butyl alcohol in a selectivity of 4.4%. No detectable amounts of CO or CO₂ were formed. The total run time for this experiment was 3.2 hours.

EXAMPLE 17

The catalyst used in Example 16 was employed in another run using the same procedure except that the gaseous feed to the reactor was 102 cc. per minute of butene-1, 730 cc. per minute of the oxygen:nitrogen gas mixture and 224 cc. per minute of water vapor. This provided a gas hourly space velocity of 6,336 cc/cc/hr. After achieving steady state conditions, methyl ethyl ketone was found to be formed in a selectivity of 92.4% at a butene conversion of 5.9%. Secondary butyl alcohol was found to be formed in the selectivity of 5.4%. No detectable amounts of CO or CO₂ were formed. The total run time for this experiment was 5.1 hours.

EXAMPLE 18 FOR COMPARISON

Run A

To illustrate the improved butene oxidation achieved by the neodymium-molybdenum catalysts of this invention, a series of runs were conducted employing a molybdenum oxide catalyst. Following the procedure of Example 16, 45 cc. of gamma-alumina (12-20 mesh; 100 m²/gm; Alfa Products) was dried in air at 250° C. for 2 hours. Then, 6.5 grams of (NH₄)₆Mo₇O₂₄.4H₂O was dissolved in distilled water to make 18 cc. of solution. The resulting solution was employed in vacuum impregnation of the dried gamma-alumina solids (37.1 grams) using the procedure of Example 16. After the vacuum impregnation, the wet solids were dried at a temperature of 125° C. for 1 hour, 250° C. for 1 hour and 350° C. for 1 hour and then calcined in nitrogen at 500° C. for 3 hours. The resulting supported MoO₃ catalyst was found to contain 9.5% of molybdenum calculated as the element, based on the total weight of the supported catalyst.

Following the procedure of Example 16, 10 cc. of the supported MoO₃ catalyst was mixed with 20 cc. of fused ceramic inerts (12-20 mesh) and was contacted with a gas feed containing 60 cc./min. 1-butene, 730 cc./min. O₂/N₂ gas mixture (10 vol. % O₂, 90 vol. % N₂) and 224 cc./min. water vapor, at a temperature of 300° C. and a gas inlet pressure of 7.1 psig, thereby using a total gas hourly space velocity of 6084 cc/cc/hr., for 2.0 hours, methyl ethyl ketone selectivity was found to be 80.6%, at a butene conversion of 9.1%. In addition, secondary butyl alcohol was formed in a selectivity of 8.1% and carbon dioxide and carbon monoxide selectivities were 6.9% and 2.8%, respectively.

Run B

In a separate run using the MoO₃ catalyst of Run A, a gas feed containing 102 cc./min. 1-butene, 730 cc./min. O₂/N₂ (10:90 vol:vol) mixture and 224 cc./min. water vapor was passed through the reactor at a total gas hourly space velocity of 6338 cc/cc/hr. and at 305° C. and 7.1 psig for 5.0 hours. At a butene conversion of 20.5%, selectivities to the following were observed: 71.0% methyl ethyl ketone, 4.2% secondary buty alcohol, 3.8 $CO_2$ and 1.9% CO.

Therefore, the Nd—Mo oxide catalyst of Examples 16 and 17 provided improved selectivities to methyl ethyl ketone and reduced selectivities to CO and $CO_2$. Comparing Example 7 and Run B of this Comparative Example 18 (which employed substantially the same total gas hourly space velocity conditions), it is seen that the Nd—Mo oxide catalyst gave a total of 97.8% selectivity to useful products, methyl ethyl ketone and secondary butyl alcohol, whereas the $MoO_3$ catalyst gave a total selectivity to these products of only 75.2%. Further, the Nd—Mo oxide catalyst of Example 17 formed no detectable CO or $CO_2$, representing a significant advantage over the $MoO_3$ catalyst of Run 18 which gave 5.7% total (CO+$CO_2$) oxides of carbon.

EXAMPLE 19

The mixture of inerts and neodymium-molybdenum oxide catalyst used in Example 17 above was contacted in the reactor with a gas mixture of hydrogen sulfide (charged as a 6% $H_2S$ in $N_2$; 190 cc./min.) and $H_2$ (230 cc./min.) at a temperature of 325° C. for 3 hours, followed by $H_2$ stripping suing pure $H_2$ (520 cc./min.) at 325° C. for 1 hour. The sulfided catalyst thus prepared was determined to contain 3.7 wt. % neodymium and 9.5 wt. % molybdenum, calculated as the respective elements.

Following the procedure of Example 16 a butene feed having the composition employed in Example 16 was passed over the sulfided catalyst at a gas hourly space velocity of 3,984 cc/cc/hr. for 5.5 hours. After achieving steady-state conditions, methyl ethyl ketone was found to have been formed in a selectivity of 91.1% butene conversion of 3.4%. Secondary butyl alcohol was formed in a selectivity of 8.9%. Thus, the butene-1 was converted in a 100% selectivity to valuable ketone and alcohol products. No CO or $CO_2$ was detected.

EXAMPLE 20

The procedure for Example 19 was repeated employing the neodumium-molybdenum sulfided catalyst of that Example, except that the gas feed to the reactor comprised 60 cc./min. of butene-1, 730 cc./min. of the oxygen:nitrogen mixture and 224 cc./min. of water vapor, thereby using a gas hourly space velocity of 6,084 cc/cc/hr., for 3.3 hours. Methyl ethyl ketone selectivity was 86.6% at a butene conversion of 8.5%.

EXAMPLE 21 FOR COMPARISON

Following the $H_2S$ sulfiding/$H_2$ stripping procedure of Example 19, the $MoO_3$ catalyst used in Comparative Example 18 was sulfided, to prepare a supported Mo sulfide catalyst containing 9.5 wt. % Mo, which was then tested using the procedure of Example 16.

Run A

In a first run, a gas feed containing 60 cc./min. 1-butene, 730 cc./min. $O_2/N_2$ (10:90 vol:vol) gas mixture and 224 cc./min. water vapor was charged to the reactor at 305° C. and 7.1 psig, using a total gas hourly space velocity of 6,084 cc/cc/hr. for 5.2 hours. At a butene conversion of 15.1%, product selectivities were: 62.6% methyl ethyl ketone, 13.6% secondary butyl alcohol, 10.0% $CO_2$ and 2.0% CO.

Run B

In a second run, the gas feed contained 102 cc./min. 1-butene, 730 cc./min. $O_2/N_2$ (10:90 vol:vol) gas mixture and 224 cc./min. water vapor, and a temperature of 298° C. and pressure of 7.1 psig were used for 6 hours. (6,338 cc/cc/hr. total gas hourly space velocity.) At a 12.6% butene conversion, product selectivities were: 68.8% methyl ethyl ketone, 9.6% secondary butyl alcohol, 5.8% $CO_2$ and 1.9% CO.

Thus, the Nd—Mo sulfide catalysts of Examples 19 and 20 provided a greatly improved selectivity to useful product compared with Mo sulfide alone. Comparing Example 20 and 21 (each used a GHSV of 6,084 cc/cc/hr.) it is seen that the Nd—Mo sulfide catalyst catalyzed the conversion of 1-butene to methyl ethyl ketone and secondary butyl alcohol in a total selectivity of 90.2%, whereas the Mo sulfide catalyst of Run 21 formed these products in a total selectivity of only 76.2%. Correspondingly, no CO or $CO_2$ was detected for the Nd—Mo sulfide catalyst of Example 20, whereas a 12.0% total (CO+$CO_2$) oxides of carbon selectivity was observed in Run 21.

EXAMPLE 22

The catalyst preparation procedure of Example 16 was repeated except that the support comprised 16-25 mesh gamma-alumina (Alfa Products; 100 $m^2$/gm.; 0.43 cc./gm pore volume). The supported Nd—Mo oxide catalyst was found to contain 3.7 wt. % Nd and 9.5 wt. % Mo, calculated as the metals.

After mixing with 16-25 mesh ceramic inerts (10 cc. of supported Nd—Mo oxide, 20 cc. of inerts), a series of runs were made using selected reaction conditions, following the procedure of Example 16. The data thereby obtained are set forth in Table VI below.

TABLE VI

| Run No. | Time (hrs) | Temp. (°C.) | Press. psig | Gas Feed (cc/min.) | | | GHSV (3) | Butene Conv. (%) | % Selectivity | | | | Total & Selec. | |
|---|---|---|---|---|---|---|---|---|---|---|---|---|---|---|
| | | | | Butene (1) | $O_2/N_2$ (2) | $H_2O$ | | | MEK (4) | $CO_2$ | CO | SBA (5) | (MEK + SBA) | ($CO_2$ + CO) |
| 1 | 0.7 | 303 | 9.3 | 60 | 380 | 224 | 3984 | 2.8 | 62.3 | 2.9 | 2.9 | 23.8 | 86.1 | 5.8 |
| 2 | 1.7 | 309 | 9.4 | 102 | 730 | 224 | 6336 | 1.6 | 73.3 | 3.6 | 3.6 | 12.5 | 85.8 | 7.2 |
| 3 | 2.8 | 307 | 9.4 | 60 | 730 | 224 | 6084 | 3.0 | 80.2 | tr. | tr. | 13.9 | 94.1 | tr. |

(1) Butene feed = 85 vol. % butene-1, 15 vol. % n-butane.
(2) 10% $O_2$ in $N_2$.
(3) Total gas hourly space velocity (cc/cc/hr.).
(4) MEK = methyl ethyl ketone.
(5) SBA = secondary butyl alcohol.

Secondary butyl alcohol selectivity was 3.6% and butyl mercaptan selectivity was 4.5%.

EXAMPLE 23

Following the $H_2S$ sulfiding/$H_2$ stripping procedure of Example 19, the neodymium-molybdenum-oxide catalyst employed in Example 22 above was sulfided with hydrogen sulfide and then employed in another series of runs using the selected reaction conditions, thereby yielding the data set forth in Table VII below.

Thus, total methyl ethyl ketone and secondary butyl alcohol selectivity in Runs 1 and 2 were 87.8% and 95.0%, respectively, and total $CO+CO_2$ selectivity in each of these two runs was only 2.8%.

TABLE VII

| Run No. | Time (hrs) | Temp. (°C.) | Press. psig | Gas Feed (cc/min.) Butene (1) | $O_2/N_2$ (2) | $H_2O$ | GHSV (3) | Butene Conv. (%) | % Selectivity MEK (4) | $CO_2$ | CO | SBA (5) | $C_4SH$ (6) |
|---|---|---|---|---|---|---|---|---|---|---|---|---|---|
| 1 | 1.2 | 309 | 9.3 | 60 | 380 | 224 | 3984 | 6.5 | 67.0 | 1.9 | 0.9 | 20.8 | 2.5 |
| 2 | 2.4 | 302 | 9.4 | 102 | 730 | 224 | 6336 | 2.5 | 80.7 | 1.4 | 1.4 | 14.3 | 1.3 |

(1) Butene feed = 85 vol. % butene-1, 15 vol. % n-butane.
(2) 10% $O_2$ in $N_2$.
(3) Total gas hourly space velocity (cc/cc/hr.).
(4) MEK = methyl ethyl ketone.
(5) SBA = secondary butyl alcohol.
(6) $C_4SH$ = butyl mercaptan.

EXAMPLE 24

The catalyst preparation procedure of Example 22 was repeated using 16–25 mesh gamma-alumina, to form a fresh Nd—Mo oxide on gamma-alumina catalyst containing 3.7 wt. % Nd and 9.5 wt. % Mo, calculated as the elements. The catalyst solids (10 cc.) were mixed with 20 cc. of 16–25 mesh fused ceramic inerts and then sulfided, using the $H_2S$ sulfiding/$H_2$ stripping procedure of Example 19. The Nd—Mo sulfide catalyst was then used in two runs, at the selected conditions, to oxidize a butene feed. The data thereby obtained are set forth in Table VIII below.

TABLE VIII

| Run No. | Time (hrs) | Temp. (°C.) | Press. psig | Gas Feed (cc/min.) Butene (1) | $O_2/N_2$ (2) | $H_2O$ | GHSV (3) | Butene Conv. (%) | % Selectivity MEK (4) | $CO_2$ | CO | SBA (5) | $C_4SH$ (6) |
|---|---|---|---|---|---|---|---|---|---|---|---|---|---|
| 1 | 1.8 | 299 | 9.3 | 102 | 730 | 224 | 6336 | 4.4 | 70.0 | 1.4 | 1.0 | 16.0 | 3.1 |
| 2 | 6.1 | 311 | 9.4 | 60 | 380 | 224 | 3984 | 4.1 | 74.8 | 4.8 | 2.4 | 11.0 | 1.2 |

(1) Butene feed = 85 vol. % butene-1, 15 vol. % n-butane.
(2) 10% $O_2$ in $N_2$.
(3) Total gas hourly space velocity (cc/cc/hr.).
(4) MEK = methyl ethyl ketone.
(5) SBA = secondary butyl alcohol.
(6) $C_4SH$ = butyl mercaptan.

EXAMPLE 25

The catalyst preparation procedure of Example 16 was repeated employing 12–20 mesh silica-alumina (Davison Chemical, Grade #979; 86% silica, 13% $Al_2O_3$; 400 m²/gm; 0.90 cc./gm pore volume), dried to a weight of 12.3 gms to form a neodymium-molybdenum oxide on silica-alumina catalyst which was found to contain 3.7 wt. % Nd and 9.5 wt. % Mo, calculated as the metals. Ten cc. of this oxide catalyst (mixed with 20 cc. of fused ceramic inerts, 12–20 mesh) were employed in a first run under the conditions reported in Table IX, Run 1.

Then the catalyst in the reactor was sulfided and $H_2$ stripped as in Example 19, and two additional runs were made using the thus prepared sulfided catalyst. The data thereby obtained are set forth in Table IX as Runs 2 and 3.

These data show that a silica-alumina support is less preferred in terms of the total selectivities to MEK and SBA and the low butene conversions. However, the catalyst also formed no detectable CO or $CO_2$ by-product, so that loss of butene to these materials was not observed.

TABLE IX

| Run No. | Time (hrs) | Temp. (°C.) | Press. psig | Gas Feed (cc/min.) Butene (1) | $O_2/N_2$ (2) | $H_2O$ | GHSV (3) | Butene Conv. (%) | % Selectivity MEK (4) | $CO_2$ | CO | SBA (5) | $C_4SH$ (6) |
|---|---|---|---|---|---|---|---|---|---|---|---|---|---|
| 1 | 1.7 | 299 | 9.7 | 60 | 380 | 224 | 3984 | 0.3 | 42.7 | 0 | 0 | 31.7 | 0 |
| 2 | 0.7 | 306 | 9.7 | 60 | 380 | 224 | 3984 | 0.6 | 27.4 | 0 | 0 | 36.0 | 7.0 |
| 3 | 1.2 | 303 | 9.7 | 102 | 730 | 224 | 6336 | 0.1 | 75.3 | 0 | 0 | 15.3 | 2.0 |

(1) Butene feed = 85 vol. % butene-1, 15 vol. % n-butane.
(2) 10% $O_2$ in $N_2$.
(3) Total gas hourly space velocity (cc/cc/hr.).
(4) MEK = methyl ethyl ketone.
(5) SBA = secondary butyl alcohol.
(6) $C_4SH$ = butyl mercaptan.

EXAMPLE 26

Using the procedure of Example 16, 30 cc. of gamma-alumina (12–20 mesh; 200 m²/gm; 0.45 cc./gm; Alfa Products) were dried at 250° C. in air for 2 hours to a dry weight of 27.2 grams, and then vacuum impregnated, successively, with aqueous solutions containing $(NH_4)_6Mo_7O_{24}$, $Nd(NO_3)_3$ and $Rh(NO_3)_2$. The first impregnation employed 10.6 cc. of an aqueous solutions containing 4.77 gms. of $(NH_4)_6Mo_7O_{24}\cdot 4H_2O$ and distilled water, and the impregnated catalyst was dried in air at 125° C. for 1 hour, 250° C. for 1 hour and 350° C.

for 1 hour and then calcined in air at 500° C. for 3 hours. A 14.55 gram portion of these solids were then impregnated with the Nd salt using 5.3 cc. of an aqueous solution containing 1.64 gms. of $Nd(NO_3)_3.6H_2O$ dissolved therein, once again followed by drying under the above four-step process. Finally, the solids were impregnated with the $Rh(NO_3)_3$ using 5.3 cc. of an aqueous solution containing 0.41 gm. of dissolved $Rh(NO_3)_3.2H_2O$, again followed by the above four-step drying and the calcining process. The resulting supported Nd—Rh—Mo oxide catalysts was found to contain 1.0 wt. % Rh, 3.7 wt. % Nd and 9.5 wt. % Mo, calculated as the metals, based on the weight of the total catalyst support.

Using the procedure of Example 16, 10 cc. of the Nd—Rh—Mo oxide catalyst was placed in the test reactor with 20 cc. of 12–20 mesh fused ceramic inerts, and a gas feed comprising 60 cc./min. of a gas mixture containing 85 vol. % 1-butene, and 15 vol. % iso-butane, 380 cc./min. of a 10:90 vol:vol $O_2:N_2$ gas mixture and 224 cc./min. of water vapor was passed to the reactor (GHSV=3,984 cc/cc/hr.) using a reactor temperature of 305° C. and a gas inlet pressure of about 9.3 psig, for 1 hour.

At a butene conversion of 14.1%, the following selectivities were found: 60.6% methyl ethyl ketone, 4.3% secondary butyl alcohol, 16.6% $CO_2$ and 8.5% CO.

EXAMPLE 27 FOR COMPARISON

To illustrate the improved results obtained with the Nd—Rh—Mo oxide catalyst of Example 26, the catalyst preparation procedure of Example 26 was repeated, except that no $Nd(NO_3)_3$ was impregnated onto the gamma-alumina which was only subjected to the sequential impregnation/drying/calcining of the Mo and Rh salts thereon. After calcining of the dried impregnated solids, 10 cc. of the resulting Mo—Rh oxide catalyst (containing 1.0 wt. % Rh and 9.5 wt. % Mo, calculated as the metals) was mixed with 20 cc. of the 12–20 mesh fused ceramic inerts and a series of runs were made using the conditions indicated in Table X below were performed.

Comparing Example 26 (conducted at 305° C.) and Run 27 (301° C.), the two closest reaction conditions, it is seen that the Rh—Mo oxide catalyst of Run 27-B provided an inferior MEK selectivity (43.8% vs. 60.6%, for the Nd—Mo—Rh oxide catalyst of Example 26) in addition to an inferior SBA selectivity and an increased selectivity loss to CO and $CO_2$ (39.1% vs. 25.1% for the Nd—Mo—Rh oxide catalyst of Example 26).

EXAMPLE 28

Following the $H_2S$ sulfiding/$H_2$ stripping procedure of Example 19, the Nd—Rh—Mo oxide catalyst of Example 26 was sulfided in the reactor and the resulting Nd—Rh—Mo sulfide catalyst was contacted with a gas feed containing 60 cc./min. of a gas mixture containing 85 vol. % 1-butene and 15 vol. % iso-butane, 380 cc./min. $O_2:N_2$ (10:90 vol:vol) gas mixture and 224 cc./min. water vapor (GHSV=3,984 cc/cc/hr.) at a temperature of 302° C. and a gas inlet pressure of 9.7 psig.

At a butene conversion of 18.5%, the following selectivities were observed: 60.4% MEK, 1.8% SBA, 20.1% $CO_2$, 3.3% CO and 6.9% butyl mercaptan.

EXAMPLE 29 FOR COMPARISON

The Rh—Mo oxide catalyst used in Comparative Example 27 was sulfided in the reactor using the procedure of Example 19 and the resulting Rh—Mo sulfide catalyst was tested for its butene oxidation activity. The run conditions and data obtained are summarized below in Table XI.

Under no conditions in Runs 29A–29C were the high MEK selectivities and low $CO+CO_2$ selectivities observed in Example 28 achieved. At the closest space velocities, the Nd—Rh—Mo sulfide catalyst of Example 28 had over a 12 percentage points advantage in MEK selectivities (60.6% vs. 48.5% for Run 29-A) and formed over 13 percentage points less in $CO+CO_2$ selectivity loss ($CO+CO_2$ selectivities=23.4% for Example 28 vs. 36.8% for the Rh—Mo sulfide catalyst of Run 29-A).

TABLE X

| Run No. | Time (hrs) | Temp. (°C.) | Press. psig | Gas Feed (cc/min.) Butene (1) | $O_2/N_2$ (2) | $H_2O$ | GHSV (3) | Butene Conv. (%) | % Selectivity MEK (4) | $CO_2$ | CO | SBA (5) |
|---|---|---|---|---|---|---|---|---|---|---|---|---|
| A | 8.9 | 250 | 7.1 | 102 | 730 | 224 | 6338 | 8.0 | 48.7 | 29.7 | 7.8 | 5.9 |
| B | 0.6 | 301 | 7.1 | 60 | 730 | 224 | 6084 | 29.3 | 43.8 | 20.9 | 18.2 | 2.5 |
| C | 5.9 | 312 | 7.1 | 102 | 730 | 224 | 6338 | 28.4 | 69.5 | 13.7 | 6.8 | 3.6 |

(1) Butene feed = 100% butene-1.
(2) 10% $O_2$ in $N_2$.
(3) Total gas hourly space velocity (cc/cc/hr.).
(4) MEK = methyl etyl ketone.
(5) SBA = secondary butyl alcohol.

TABLE XI

| Run No. | Time (hrs) | Temp. (°C.) | Press. psig | Gas Feed (cc/min.) Butene (1) | $O_2/N_2$ (2) | $H_2O$ | GHSV (3) | Butene Conv. (%) | % Selectivity MEK (4) | $CO_2$ | CO | SBA | $C_4SH$ (5) |
|---|---|---|---|---|---|---|---|---|---|---|---|---|---|
| A | 4.2 | 300 | 7.1 | 31 | 380 | 112 | 3138 | 36.3 | 48.5 | 31.5 | 5.3 | 0 | 0 |
| B | 6.4 | 302 | 7.1 | 102 | 730 | 224 | 6338 | 18.4 | 48.1 | 26.2 | 8.5 | 0 | 0 |
| C | 2.4 | 310 | 7.1 | 60 | 730 | 224 | 6084 | 46.9 | 58.6 | 12.7 | 6.2 | 0.6 | 0 |

(1) Butene feed = 100 vol.% butene-1.
(2) 10% $O_2$ in $N_2$.
(3) Total gas hourly space velocity (cc/cc/hr.).
(4) MEK = methyl ethyl ketone.
(5) Butyl mercaptan.

EXAMPLE 30

The procedure for Comparative Example 29 was repeated employing the Nd—Rh—Mo sulfided catalyst of that Example, except that the reaction temperature was 310° C. and the gas feed to the reactor did not include the oxygen:nitrogen gas mixture: 380 cc./min. of $N_2$ was used instead. A total gas hourly space velocity of 3,984 cc/cc/hr. was used for a run time of 4.0 hours. Methyl ethyl ketone selectivity was 93.7% at a butene conversion of 3.0%, secondary butyl alcohol selectivity was 4.3%, and selectivity to butyl mercaptan was 2.0%. No CO or $CO_2$ by-products were detected.

EXAMPLE 31

The procedure of Example 30 was repeated except that the reaction temperature used was increased to 365° C., at a gas hourly space velocity of 3,984 cc/cc/hr. for 6.6 hours. At a butene conversion of 2.0%, methyl ethyl ketone selectivity was observed to be 95.0 percent and selectivity to secondary butyl alcohol was 2.5%. Selectivity to butyl mercaptan was 2.5% and no CO or $CO_2$ by-products were detected.

As is seen from these data, the ketone product was formed in a selectivity of from about 94 to 95 percent in the absence of molecular oxygen. In addition, the alcohol product was formed in a selectivity of 4.3 and 2.5 percent at a temperature of 310° and 365° C. respectively. Since the catalyst comprised a sulfide catalyst of this invention, the oxygen molecules incorporated into the ketone and alcohol products are believed to have been derived from the water vapor introduced with the gas feed. Surprisingly, no detectable amounts of carbon dioxide or carbon monoxide were formed as by-products, thereby removing the significant disadvantage of prior art methods in which these oxides of carbon were formed in large amounts as by-products. The example illustrates the process of this invention can employ in an $O_2$-free reaction zone, a temperature of reaction in excess of the level at which carbon dioxide and CO begin to be formed when using a gas feed containing molecular oxygen.

Finally, lower butyl mercaptan selectivities resulted when molecular oxygen-containing gas was not used, providing surprisingly decreased sulfur-containing by-products in the absence of $O_2$.

EXAMPLE 32

The procedure of Example 31 was repeated employing the neodymium-rhodium-molybdenum catalyst used in that Example, except that the nitrogen gas was omitted from the gas feed to the test reactor. In this experiment, a temperature of 370° C. and a gas inlet pressure of 8.8 psig was employed (for 7.8 hours) at a total gas hourly space velocity of 1,704 cc/cc/hr., using a gas feed comprising 60 cc./min. of a butene gas mixture (containing 85 vol. % 1-butene and 15 vol. % isobutane) and 224 cc./min. of water vapor. At a butene conversion of 2.3%, product selectivity to a methyl ethyl ketone was observed to be 96.8% and secondary butyl alcohol selectivity was found to be 1.6%. In addition, butyl mercaptan was formed in an amount of 1.1%. No detectable amounts of carbon dioxide or carbon monoxide were found as by-product.

EXAMPLE 33

Using the procedure of Example 16, 16 cc. of the gamma-alumina (12–20 mesh) was dried under air at 500° C. for 3 hours to provide a dry weight of 14.1 grams. The dried catalyst support was then impregnated using 5.3 cc. of an aqueous solution containing 3.34 grams of $Nd(NO_3)_3.6H_2O$, after which the impregnated solids were dried at 125° C. for 1 hour, 250° C. for 1 hour, and 350° C. for 1 hour, in air, and then calcined in air at 500° C. for 3 hours. The resulting neodymium oxide catalyst was found to contain 7.7 wt. % of neodymium, calculated as the element, based on the weight of the catalyst support.

Twenty cc. of fused ceramic inerts (12–20 mesh) was mixed with 10 cc. of the oxide catalyst and then tested as in Example 30, employing a reaction temperature of 309° C., gas inlet pressure of 9.2 psig and a gas feed containing 60 cc./min. of a gas mixture containing 85 vol. % butene-1 and 15 vol. % isobutane, 380 cc./min. of a gas mixture comprising 10 vol. % oxygen and 90 vol. % nitrogen, and 224 cc./min. of water vapor, for a gas hourly space velocity of 3,984 cc/cc/hr., and for a run time of 1.0 hour. At a butene conversion of 2.0%, product selectivities were as follows: methyl ethyl ketone 80.7%, secondary butyl alcohol 6.8%, and carbon dioxide 10.0%. No carbon monoxide was detected.

In a separate run, the oxide catalyst used as above was sulfided in the reactor using the procedure of Example 28. A separate run was then made using the resulting neodymium sulfide catalyst for a period of 10.5 hours at a reaction temperature of 376° C. and a gas inlet pressure of 9.2 psig. The gas feed to the reactor contained 60 cc./min. of a gas mixture containing 85 vol. % butene-1 and 15 vol. % isobutane, 380 cc./min. of $N_2$ and 224 cc./min. of water vapor, for a gas hourly space velocity of 3,984 cc/cc/hr., and for a run time of 10.5 hours. At a butene conversion of 1.6%, methyl ethyl ketone selectivity was found to be 88.4%. No secondary butyl alcohol product, or carbon dioxide or carbon monoxide by-products, was detected.

EXAMPLE 34

LANTHANUM CATALYST PREPARATION

Gamma-alumina (22 cc; 12–20 mesh; 100 $m^2$/gm surface area; 0.45 cc./gm pore volume; Alfa Products) was dried in a Linberg furnace at 500° C. in air for 3.0 hours to a dry weight of 18.43 grams, and then placed into a 125 cc. filtering flask equipped with a side arm for pulling a vacuum. The solids were vacuum impregnated, successively, with aqueous solutions containing $(NH_4)_6Mo_7O_{24}$, $La(NO_3)_3$ using a 60 cc. dropping funnel attached to the filtering flask using a rubber stopper. The filtering flask was evacuated to −15 in Hg. The first impregnation employed 7.4 cc. of an aqueous solution containing 3.23 gms of $(NH_4)_6Mo_7O_{24}.4H_2O$ in distilled water, which solution was added dropwise to completely wet the solids. The impregnated catalyst was placed in a stainless steel gauze boat and dried in air at 125° C. for 1 hour, 250° C. for 1 hour and 350° C. for 1 hour and then calcined in air at 500° C. for 3 hours. After allowing the solids to cool to room temperature, these solids were then impregnated with the La salt using 7.4 cc. of an aqueous solution containing 2.17 gms of $La(NO_3)_3.6H_2O$ dissolved therein, once again followed by drying and calcining using the above four-step process. The resulting supported La—Mo oxide catalysts was found to containg 3.7 wt. % La and 9.5 wt. % Mo, calculated as the metals, based on the weight of the total catalyst support.

Ten cc. of the La—Mo oxide catalyst prepared in Example 34 was well mixed with 20.0 cc. of fused ceramic inert (12–20 mesh) and loaded into a test reactor which comprised a 24 inch (0.38 inch - ID) stainless steel tubular reactor equipped with gas inlet and gas outlet at opposing ends of the tubular reactor. The reactor was then heated to a temperature of 325° C. (which was maintained by means of an electric heating tape and a Gardsman temperature control). Temperatures in the reactor were determined by use of a thermocouple positioned in the center of the catalyst bed. The oxide solids were sulfided by passing to the reactor a gas mixture of $H_2S$ (charged as a 6% $H_2S$ in $N_2$; 190 cc/min.) and $H_2$ (230 cc./min.) for three hours, followed by $H_2$ stripping using pure $H_2$ (520 cc./min.) at 325° C. for 1 hour. The sulfided catalyst was also determined to contain 3.7% La and 9.7% Mo, calculated as the elements.

EXAMPLE 35

A gaseous mixture containing 1-butene, nitrogen, and water vapor was then passed to the reactor at a gas hourly space velocity of 3,984 cc/cc/hr., and at the following feed rates: 60 cc./min. of a gas mixture containing 85 vol. % butene-1, and 15 vol. % iso-butane, 380 cc./min. of nitrogen and 224 cc./min. of water vapor. A gaseous inlet pressure of 61 Kpa was employed throughout the reaction. A gaseous effluent was continuously withdrawn from the reactor and was sampled and analyzed by means of an on-line gas chromatograph. After achieving steady state conditions, butene-1 conversion was found to be 1.3% and the following selectivities were observed: 99.0% methyl ethyl ketone and 1.0% secondary butyl alcohol. No by-product CO or $CO_2$ was detected. The total run time for the experiment was 5.2 hours.

EXAMPLE 36

The butene feed procedure of Example 35 was repeated employing the La—Mo sulfided catalyst of that Example, except that the reaction temperature was 368° C. and the gas feed to the reactor did not include the nitrogen. A total gas hourly space velocity of 1,704 cc/cc/hr. was used for a run time of 6.2 hours, employing a feed comprising 224 cc./min. water vapor and 60 cc./min. of the iso-butane/butene-1 gas mixture. Methyl ethyl ketone selectivity was 98.8% at a butene conversion of 1.5%, and secondary butyl alcohol selectivity was 1.1%. No CO or $CO_2$ by-products were detected.

In each of the foregoing examples illustrative of the process of this invention, butane by-product was observed to be formed from the butene feeds in selectivities of less than about 0.5 mol. %, based on the butene fed to the reactor. Thus, the improved process of this invention allows the formation of the desired ketone in the substantial absence of olefin hydrogenation by-products, that is, the hydrogenation by-products will be generally formed in a selectivity of less than about 1 mol. %, based on the olefin fed.

Preferably, monoolefin feeds to the process of this invention are substantially free (e.g., contain less than 1 wt. %) of diolefins or acetylenic hydrocarbons to obtain the highest catalyst activity to form the ketones corresponding to the monoolefin feeds.

It will be obvious that various changes and modifications may be made without departing from the invention and it is intended, therefore, that all matter contained in the foregoing description shall be interpreted as illustrative only and not limitative of the invention.

What is claimed is:

1. A process for preparing ketones which comprises contacting the corresponding olefin in the gaseous phase with water vapor in a reaction zone at elevated temperature in the presence of a catalyst selected from the group consisting of at least one sulfide of Ce, Nd and La, said olefin comprising at least one member selected from the group consisting of linear mono-olefins of from 2 to 20 carbon atoms and cyclic mono-olefins of from 3 to 20 carbon atoms.

2. The process according to claim 1 wherein said catalyst additionally comprises at least one promoter selected from the group consisting of sulfides of Group VIB and Group VIII noble metals.

3. The process according to claim 1 wherein said catalyst comprises a mixture of (1) a sulfide of at least one of Ce, Nd and La, (2) a sulfide of Cr, Mo or W, and (3) a sulfide of Ru, Rh, Pd, Os, Ir or Pt.

4. The process according to claim 1 wherein the olefin comprises a member selected from the group consisting of alkenes having from 2 to 20 carbon atoms and cycloalkenes having from 3 to 20 carbon atoms.

5. The process according to claim 1 wherein said olefin comprises an alkene of from 4 to 10 carbon atoms or a cycloalkene of from 4 to 10 carbon atoms.

6. The process according to claim 1 wherein said olefin is contacted with said water vapor in a reaction zone in the substantial absence of free halide.

7. The process according to claim 1 wherein said olefin and water vapor are contacted in said reaction zone in the additional presence of molecular oxygen.

8. The process according to claim 1 wherein said reaction zone is substantially free of molecular oxygen.

9. A process for converting an olefin selected from the group consisting of alkenes having from 4 to 10 carbon atoms and cycloalkenes having from 4 to 10 carbon atoms into the corresponding ketone, which comprises contacting said olefin in the gaseous phase with water vapor in a reaction zone in the presence of a solid sulfided catalyst comprising a member selected from the group consisting of Ce sulfides, Nd sulfides and La sulfides, at a temperature of from about 125° to 600° C. and at pressures of from about 0 to 2000 psig.

10. The process according to claim 9 wherein said water vapor and said olefin are introduced into said reaction zone in a molar ratio of olefin:water vapor of from about 2:1 to 1:20.

11. The process according to claim 9 wherein said catalyst additionally comprises at least one promoter selected from the group consisting of sulfides of Cr, Mo, W, Ru, Rh, Pd, Os, Ir and Pt.

12. The process according to claim 9 wherein said olefin and water vapor are contacted in the additional presence of molecular oxygen in an olefin:oxygen molar ratio of from about 0.5:1 to 10:1, based on the gases introduced to said reaction zone.

13. The process according to claim 10 wherein said olefin comprises butene-1 and said ketone comprises methyl ethyl ketone.

* * * * *